United States Patent [19]

Fink et al.

[11] Patent Number: 4,542,175

[45] Date of Patent: Sep. 17, 1985

[54] METHOD FOR THICKENING AQUEOUS SYSTEMS

[75] Inventors: Herbert Fink, Bickenbach; Klaus Huebner; Gerhard Markert, both of Ober-Ramstadt-Eiche; Norbert Suetterlin, Ober-Ramstadt, all of Fed. Rep. of Germany

[73] Assignee: Röhm GmbH, Darmstadt, Fed. Rep. of Germany

[21] Appl. No.: 522,524

[22] Filed: Aug. 12, 1983

Related U.S. Application Data

[63] Continuation-in-part of Ser. No. 329,765, Dec. 11, 1981, abandoned, which is a continuation-in-part of Ser. No. 177,587, Aug. 13, 1980, abandoned.

[30] Foreign Application Priority Data

Aug. 23, 1979 [DE] Fed. Rep. of Germany ....... 2934086
Dec. 24, 1980 [DE] Fed. Rep. of Germany ....... 3049178

[51] Int. Cl.$^4$ ................................................. C08J 3/06
[52] U.S. Cl. ...................................... 524/516; 524/555
[58] Field of Search ................. 524/516, 521, 548, 555

[56] References Cited

U.S. PATENT DOCUMENTS

| | | | |
|---|---|---|---|
| 3,300,429 | 1/1967 | Glavis | 524/516 |
| 3,356,627 | 12/1967 | Scott | 260/29.6 |
| 3,432,454 | 3/1969 | Hibbard | 260/29.6 |
| 3,575,881 | 4/1971 | Atkins et al. | 252/316 |
| 3,947,396 | 3/1976 | Kangas | 260/29.3 |
| 4,396,734 | 8/1983 | Williams | 524/548 |

FOREIGN PATENT DOCUMENTS 1393374 5/1975 United Kingdom .
2043081 10/1980 United Kingdom .

OTHER PUBLICATIONS

"The Theory of Resonance", Wheland, John Wiley and Sons, Inc., New York, p. 178.
"Advanced Organic Chemistry", Fieser and Fieser, Reinhold, New York, p. 519.
"The Encyclopedia of Chemistry", Hampel, Van Nostrand Reinhold, New York p. 63.
Chem. Ber. 90, 1437-1438 (1957).

*Primary Examiner*—Paul R. Michl
*Attorney, Agent, or Firm*—Curtis, Morris & Safford

[57] ABSTRACT

What is disclosed is a method for thickening aqueous systems in the acid range at a pH below 7 by the addition of an aqueous dispersion of a synthetic polymer having a molecular weight of at least 500,000, and which is water soluble or at least colloidally dispersible at a pH below 7, said polymer comprising (A) 5-100 percent by weight of at least one monomer having at least one basic nitrogen atom (B) 0-95 percent by weight of at least one monomer which has at most limited solubility in water, and (C) 0-30 percent by weight of at least one further non-basic, water soluble comonomer.

15 Claims, No Drawings

METHOD FOR THICKENING AQUEOUS SYSTEMS

This application is a continuation-in-part application of pending application Ser. No. 329,765, filed Dec. 11, 1981 and now abandoned, which in turn is a continuation-in-part of application Ser. No. 177,587 filed Aug. 13, 1980 and now abandoned.

The present invention relates to a method for thickening an aqueous system by combining said system with an aqueous dispersion of a synthetic polymer of a particular composition.

Such a method of thickening is known in the prior art involving the conversion of carboxyl groups, present in an emulsion polymer under neutral or acid conditions, into their salt form by the addition of an alkali.

Emulsion polymers having a thickening effect are added to aqueous systems to increase their viscosity. Because of their low viscosity, dispersions of these polymers, even having a solids content of up to 60 percent by weight, can be uniformly distributed in low-viscosity aqueous systems, for example synthetic resin dispersions used for coating purposes, by simple stirring. By the addition of a base, the viscosity of the aqueous system can be adjusted to the desired value within the shortest possible time. In contrast, the thickening of aqueous systems with dissolved or powdered high molecular weight thickening agents, for example cellulose ethers, is laborious and time consuming.

Well known examples of this kind of emulsion polymer having a thickening effect in the alkaline region are copolymers of acrylic acid with lower esters of acrylic acid and, optionally, methacrylic acid. H. Wesslau, in Makromolekulare Chemie 69, 220–240 (1963) has described the dependence of the thickening effect of such emulsion polymers on different factors, of which the softening temperature and the hydrophilicity of the polymer are the most important. The hydrophilicity is not solely determined by the content of acrylic acid units, but is influenced to a substantial degree by the "hydrophilicity" of the comonomers polymerized therewith. Whereas emulsion polymers comprising 5 percent of acrylic acid and 95 percent of ethyl acrylate can be highly thickened, those emulsion polymers containing the same amount of n-butyl acrylate instead of ethyl acrylate have only a weak thickening effect, and such polymers containing styrene instead of ethyl acrylate do not thicken at all. The small or absent ability to thicken is attributable in the first case to the low hydrophilicity of the comonomers and in the second case is additionally attributable to the high softening temperature of the polymer.

The prior art emulsion polymers taught in DE-AS No. 1,109,132 contain from 10 to 30 percent by weight of acrylic acid or methacrylic acid monomer units in addition to monomers of acrylic acid esters or methacrylic acid esters. On the addition of a base, the highly fluid milky dispersion is converted into a viscous aqueous solution. Aqueous systems can be thickened in a simple manner by mixing them with a highly fluid dispersion of this type and by the addition of a base to establish a pH value in the alkaline region, at which value the polymer containing carboxyl groups is converted into its anionic salt form and is soluble or at least colloidally dispersible.

In addition to the limitation of their use in alkaline systems, thickening agents containing carboxyl groups have the further disadvantage that they form relatively hard films and the film hardness of soft synthetic resin dispersions thickened therewith is clearly increased by their use.

To be sure, it is not always desirable that the thickened aqueous system be alkaline. For example, polymeric thickening agents having a thickening effect which is independent of the pH value are described in German Pat. No. DE-PS 10 37 407. They contain units of quaternized aminoalkyl esters of polymerizable carboxylic acids. However, because the polymers can be swollen in the entire pH region, low viscosity dispersions which can be thickened cannot be prepared from such polymers.

Corresponding emulsion polymers having a thickening effect for acid aqueous systems have heretofore not been known although they have been desired for the adjustment of viscosity. For example, self-cross linking synthetic resin dispersions are as a rule used in an acid milieu because their cross-linking is acid catalyzed. Thus, aqueous synthetic resin dispersions are desirably used in a thickened form for textile finishing. However, resins of this type must be adjusted to an acid pH if they contain either self-crosslinking groups or are condensation resins which crosslink only in the acid region. In these cases, dispersions of polymers containing carboxy groups could not be used as thickening agents.

The present inventors have set themselves the task of developing a method for thickening aqueous systems which can also be used if the thickened aqueous system is acidic. The task is accomplished by the method of the invention, which comprises thickening an aqueous system by combining it with an aqueous dispersion of a polymer comprising (A) 5–100 percent by weight of an unsaturated free-radically polymerizable monomer having at least one nitrogen atom, (B) 0–95 percent by weight of an unsaturated free-radically polymerizable comonomer which is insoluble in water or has at most limited solubility in water, and (C) 0–30 percent by weight of an unsaturated free-radically polymerizable comonomer which is non-basic and is water soluble.

The polymer has a molecular weight of at least 500,000 and is water soluble or at least colloidally dispersible at a pH value below 7. The aqueous systems combined with such a polymer dispersion thicken at pH values below 7.

The thickening effect of the dispersions used according to the invention is attributable to the basic nitrogen atom of monomer component (A). In the acid region, this nitrogen atom is present in the form of the corresponding ammonium salt. The hydrophilicity of the ammonium salt is significantly greater than that of the corresponding amino group and increases the hydrophilicity of the entire polymer. The appearance of the thickening effect depends on a series of conditions, which are summarized below.

1. In component A, at least one nitrogen atom must be present which converts to the salt form in the acid region. If this condition is fulfilled, there is a "basic nitrogen atom" present according to the terms of the present invention. The $pK_b$-value of the corresponding monomers should preferably be in the region from 3 to 6.

2. The synthetic polymer, in its basic form, must be so slightly hydrophilic that it is insoluble in the aqueous phase of the dispersion or at most is slightly swellable by water: otherwise it cannot be present in a dispersed condition.

3. The synthetic polymer must be so strongly hydrophilic in the acid region, after conversion into the salt form, that it is truly dissolved or is at least colloidally dispersed. The colloidal dispersions are outwardly distinguished form true solutions by a weak Tyndall effect, i.e. a slight scattering of incident light, and physically by incomplete hydration and extension of the macromolecules. Colloidally dispersed polymers are essentially present in the form of strongly swollen submicroscopic particles.

4. The polymer in the salt form, either in the genuine dissolved or colloidally dispersed condition, must have a thickening effect, for which a molecular weight of at least 500,000, and preferably more than one million, is necessary. A highly branched structure, which can extend almost to the limits of crosslinking, is particularly advantageous and is attainable by the inclusion, in the structure of the polymer, of small amounts of crosslinking agents. As branching or crosslinking increases, there is a transition from a genuinely dissolved to a colloidally dispersed condition. With too strong a degree of crosslinking, the swellability and colloidal dispersibility of the polymer are lost.

Polymer dispersions which meet all the aforementioned requirements are milk-like in the neutral or alkaline region and are thinly fluid, while in the acid region they are highly viscous and clear. They can be mixed with an aqueous system to be thickened which is already acid, in which case the combination will thicken within a few seconds or minutes. In general, the aqueous disperion, which may optionally be diluted beforehand, is stirred into the aqueous system. However, this procedure can also be reversed. If the aqueous system to be thickened is not acid when mixed with the disperion, the combination retains its initial viscosity and first thickens upon acidification.

As aqueous systems which can be thickened according to the present invention, pure water and all aqueous mixtures which contain water as an essential component are encompassed. In general, the systems contain at least 20 percent by weight of water and, preferably, more than 50 percent by weight of water. In addition to water, other liquid components may be present in the aqueous system, above all water-miscible organic liquids such as lower alcohols, glycols, glycerine, ketones, lower carboxylic acids, formamide, acetamide, dimethylsulfoxide, tetrahydrofuran, and dioxan, inter alia. The aqueous phase may also contain organic or inorganic solid substances dissolved there, for example urea, sugar, soaps, emulsifiers, inorganic salts or acids, or macromolecular substances such as proteins, cellulose ethers, or synthetic water soluble polymers.

The aqueous system to be thickened may contain water insoluble components and form suspensions, emulsions, or colloids with these components. The thickening of aqueous synthetic resin dispersions is a preferred field of use of the method of the invention. The aqueous system can also, in turn, be emulsified in a non-aqueous medium. In this case, only the emulsified aqueous system within the emulsified droplets can be thickened according to the present invention, but not, generally, the non-aqueous emulsion per se.

Any detectable increase in the viscosity of the aqueous system is designed as "thickening". In many cases, a small increase in viscosity, e.g. one effecting the conversion of a turbulently streaming aqueous medium to laminar flow, is sufficient. The aqueous system can already be present initially in a thickened state and thickened according to the invention to reach a still higher viscosity. In general, one speaks of "thickening" as occurring only if the measurable viscosity increases by at least 10 percent over its initial value. At low initial viscosities, the thickening is only then detectable and of significance from the view point of technical use if the product of the initial viscosity (measured in mPa.s) multiplied by the increase in viscosity (expressed in percent) attains or exceed a value of 1,000. This is illustrated by the following numerical examples:

| Initial Viscosity | Final Viscosity | Percentage Increase in Viscosity | Product of Initial Viscosity × Increase in Viscosity |
| --- | --- | --- | --- |
| 1 mPa · s | 11 mPa · s | 1000 | 1000 mPa · s |
| 10 mPa · s | 20 mPa · s | 100 | 1000 mPa · s |
| 100 mPa · s | 110 mPa · s | 10 | 1000 mPa · s |
| 1000 mPa · s | 1100 mPa · s | 10 | 10000 mPa · s |

As a rule, a final viscosity of at least 100 mPa.s is sought for. Typical thickened aqueous systems have viscosity values in the region from 1000 to 15000 mPa.s at room temperature.

The aqueous systems thickened according to the present invention must be contrasted with those which contain small amounts of water soluble polymers for the purpose of flocculation or the acceleration of sedimentation, which polymers do not bring about any detectable increase in viscosity.

The amount of dispersed polymer necessary for thickening depends on its efficacy and on the final viscosity which is desired. Often it lies in the range from 0.1 or 0.5 to 10 percent, and preferably in the range from 1 to 3 percent, of pure polymer by weight of the water in the aqueous system. In many cases, thickening of the aqueous system does not occur at room temperature after addition of the aqueous dispersion, even if the system is made acid, but first occurs when the combination is warmed. On cooling, the thickening effected by such heating generally persists.

Thickening occurs at a pH value at which the basic nitrogen atoms present in the synthetic polymer are converted to the ammonium salt form. As a rule, this occurs already at pH values very closely below 7. As a result of a certain buffer effect of the polymer, the full thickening effect first occurs at pH values below 5. In general, no further thickening is any longer effected below a pH of 3. In practice, the pH range of the thickened aqueous system is most often in a preferred range between 2.0 and 5.5.

Monomer component (A) of the synthetic polymer must have at least one carbon-carbon double bond capable of free radical polymerization or, at least, copolymerization, particularly in the form of a vinyl, vinylidene, or vinylene group, and at least one basic nitrogen atom in the form of a secondary or tertiary amino group which optionally may also be part of a ring system. Primary amino groups are generally less suitable than are secondary amino groups, which in turn are less suitable than tertiary amino groups, because they disturb the polymerization. Examples of suitable monomers are N-vinyl-imidazole, N-vinyl-imidazoline, N-vinyl-imidazolidine, 4-vinyl-pyridine, and the N-substituted amides of $\alpha,\beta$-unsaturated polymerizable monocarboxylic or dicarboxylic acids having at least one basic nitrogen atom in the N-substituent.

Because of their outstanding thickening effect, the esters of α,β-unsaturated polymerizable monocarboxylic or dicarboxylic acids having at least one basic nitrogen atom in the alcohol portion are preferred as component (A). The acrylic acid esters and methacrylic acid esters are particularly preferred. Further, esters of maleic, fumaric, and itaconic acid are mentioned. The aforementioned esters have the structure

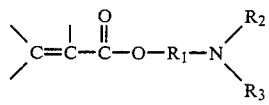

wherein groups $R_1$, $R_2$, and $R_3$ together preferably contain at least 5 carbon atoms, and groups $R_2$ and $R_3$, taken together with the nitrogen atom to which they are attached, can form a 5- or 6-membered nitrogen- or nitrogen/oxygen-containing heterocyclic ring system. Those esters which contain an ethylene group as $R_1$ give dispersions which have a tendency to thicken even above a pH of 7 and, to be sure, tend all the more to thicken the smaller the total alcohol portion of the ester is. For this reason, dispersions of polymers containing dimethylaminoethyl methacrylate, which has only four carbon atoms in the alcohol group, are not among the preferred embodiments of the invention. Esters of the aforementioned structure having five or more carbon atoms can be derived from 3-dialkylamino-2,2-dimethyl propanols such as 3-dimethylamino-2,2-dimethyl propanol, from N,N-diethylaminoethanol, N-butylaminoethanol, N,N-dipropylaminoethanol, 2-piperidino-ethanol, 2-(4-morpholinyl)-ethanol, 2-(N-imidazolyl)-ethanol, or from 2-piperazino-ethanol. Preferably, group $R_1$ has at least three carbon atoms, for example such as in esters of 3-dimethylamino-2,2-dimethyl propanol, of 2-dimethylamino-1-propanol, or of dimethylamino-isopropanol, and particularly preferably have at least three carbon atoms in a straight chain between the ester oxygen atom and the basic nitrogen atom. Examples of the latter particularly preferred esters are 3-dimethylaminopropyl-acrylate and -methacrylate (and the corresponding 3-diethylamino-propyl compounds) and 4-dimethylaminobutyl-acrylate and -methacrylate.

Preferred amides and esters of acrylic and methacrylic acid have the formula

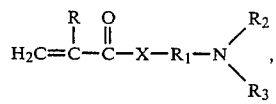

wherein R is hydrogen or methyl; X is oxygen or —NH—; $R_1$ is lower alkylene having 2 to 4 carbon atoms; $R_2$ and $R_3$, taken alone, are lower alkyl having 1 to 4 carbon atoms such that $R_1$, $R_2$, and $R_3$, together contain at least 5 carbon atoms; and wherein $R_2$ and $R_3$, taken together with the nitrogen atom to which they are attached, can form a 5- or 6-membered nitrogen- or nitrogen/oxygen-containing ring.

Homopolymers of the monomer (A) are suitable as synthetic polymers for the present invention to the extent that they meet the requirements earlier described. However, that is not always the case, for example if the homopolymers are already soluble in the alkaline pH region or have $T_{\lambda max}$-values above 100° C.

Thus, copolymers are often employed which in addition to component (A), contain units of weakly water soluble monomers (B), or readily water soluble monomers (C), or of both. Monomers having a water solubility of at most 10 percent at 20° C. are considered to be monomers having "at most limited solubility" in water. They can be present in amounts of up to 95 percent by weight of the synthetic polymer and preferably are present in amounts from 50 to 80 percent by weight. The alkyl esters of acrylic and methacrylic acids, such as the methyl-, ethyl-, n-propyl-, isopropyl-, n-butyl-, sec. butyl-, hexyl-, cyclohexyl-, 2-ethylhexyl-, octyl-, and dodecyl-esters; vinyl esters such as vinyl-acetate, -propionate, -butyrate, and -hexoate; vinyl ethers such as methyl-, ethyl-, or butyl-vinyl ethers; styrene; acrylonitrile and methacrylonitrile; ethylene; propylene, and the like belong to this group.

The hydrophilicity of the emulsion polymer can be increased, if necessary, by the presence of minor amounts of the water soluble comonomers (C), not amounting to more than 30 percent by weight of the synthetic polymer. These comonomers have a water solubility of more than 10 percent by weight at 20° C. To this group belong, for example, hydroxyalkyl acrylates and methacrylates having 2 to 4 carbon atoms in the hydroxylalkyl portion such as hydroxyethyl- acrylate and -methacrylate, acrylamide and methacrylamide, vinyl pyrrolidone, and comonomers having quaternary ammonium groups such as methacryloxyethyl-trimethyl-ammonium chloride. Comonomers having carboxyl or carboxylate groups, such as acrylic, methacrylic, maleic, fumaric, and itaconic acids and their water soluble salts, can in many cases have a disadvantageous effect on the thickening properties because of mutual interaction with the basic nitrogen atom. Thus, the preferred polymers of the present invention are those which are completely free of carboxyl and all other acid groups, i.e. are comprised solely of basic monomers (A) and neutral monomers (B) and (C), all free of acid groups.

The monomers of groups (A), (B), and (C) cannot be chosen arbitrarily. Rather, their choice requires a careful mutual balancing in order to meet the aforementioned requirements. This is particularly true for the adjustment of overall hydrophilicity in the acid and alkaline regions and of the dynamic freezing point, $T_{\lambda max}$.

Monomers (A) should in general be relatively hydrophilic. That is, their water solubility at 20° C. can be above or below 10 percent. A larger proportion of these monomers effects a strong thickening action.

Like the monomers of group (A), the water soluble comonomers (C) increase the hydrophilicity of the polymers and, to be sure, increase it all the more the greater their water solubility. The monomers of group (B), on the other hand, decrease hydrophilicity. This effect is all the more pronounced as more or larger hydrophobic groups are present in the monomers. Aliphatic groups having 4 or more carbon atoms, as well as aromatic groups, have a strongly hydrophobizing effect. Materials carrying such groups are, for example, styrene and the butyl-, hexyl-, or octyl-esters of unsaturated carboxylic acids. In contrast, the corresponding methyl-, ethyl-, and propyl-esters, vinyl esters of lower fatty acids, and acrylonitrile or methacrylonitrile have only a weak hydrophobizing effect.

The dynamic freezing point, $T_{\lambda max}$ (determined according to DIN 53 445) can be very exactly adjusted in a known fashion by a choice of the mixing ratios of "hard" and "soft" monomers and should in general be below 100° C. "Hard" monomers are those which form homopolymers having a high dynamic freezing point or having a high glass transition temperature. Of the monomers suitable for use as component (A), those having an amide structure are "hard". "Hard" monomers of group (B) are, above all, the lower methacrylic acid esters, acrylonitrile and methacrylonitrile, and styrene. "Hard" monomers falling within group (C) are the amides of acrylic acid and methacrylic acid and, to the extent they can be used, the acids themselves.

Among the "soft" monomers are, in particular, the lower acrylic acid esters, namely methyl-, ethyl-, and n-propyl-acrylate, because they have little hydrophobicity and at the same time permit the preparation of soft hydrophilic copolymers.

Other soft comonomers, such as the higher esters of acrylic acid and methacrylic acid, from the butyl esters upwards, reduce softening temperature and hydrophilicity at the same time. Synthetic polymers having a dynamic freezing point below 20° C. have a high thickening effect at room temperature and are preferred for this reason.

The "hardness" of numerous monomers, expressed in terms of the glass transition temperature of the hompolymer, is given in the "Polymer Handbook" of Brandrup and Immergut, pages III/139–192 (1975). The harmonizing of polymer properties by the admixture of different comonomers is all the more successful the more similar is their polymerization behavior. The aforementioned "Polymer Handbook" contains numerical values (Q,e) relating to such behavior for many monomers (pages II/387–404). The derivatives of acrylic acid and of methacrylic acid behave particularly advantageously from this point of view so that it is recommended to choose the monomers of all three groups, (A), (B), and (C) entirely or predominantly from such derivatives.

Since the thickening effect increases with increasing molecular weight of the synthetic polymer, all influences which have a tendency to lower molecular weight should be excluded as much as possible. Additives having a chain-transfer effect and too high a stream of free radicals during polymerization should be avoided.

The thickening effect is promoted by the presence of small amounts of crosslinking agents. Monomers having two or more free-radically polymerizable groups are to be understood as being among such agents. They are preferably present in the structure of the synthetic polymers in amounts from 0.01 to 0.5 percent by weight. Exemplary of suitable crosslinking agents are ethyleneglycol-diacrylate or -dimethacrylate, 1,2-propylene glycol-diacrylate or -dimethacrylate, butanediol-1,4-diacrylate or -dimethacrylate, methylene-bis-acrylamide or -bis-methacrylamide, and divinylbenzene.

The synthetic polymers can be prepared according to known methods for aqueous emulsion polymerization. As emulsifiers, conventional emulsifiers having non-ionic, cationic, anionic, or amphoteric properties can be used in the usual amounts, which for example are between 0.01 and 10 percent by weight of the aqueous phase. A possible disturbing interaction between the basic nitrogen atoms of the monomer component (A) and anionic emulsifiers can be avoided by decreasing the amount of anionic emulsifiers or by the use of cationic or non-ionic emulsifiers or mixtures thereof. As examples of emulsifiers which can be used, sodium lauryl sulfate, sodium dodecyl benzene sulfonate, stearyl dimethyl-benzyl-ammonium chloride, coco fatty amine hydrochloride, oxyethylation products of alkylphenols, of fatty alcohols, or of fatty acids with about 20–100 mols of ethylene oxide units, and amphoteric surface agents can be mentioned.

For preparing the emulsion polymers, the monomers may be present in emulsified form with the necessary auxiliary agents and polymerization may then be initiated. However, in general it is preferred that the monomers, as such or in the form of an aqueous emulsion, be added gradually during the course of the polymerization method. For initiating the polymerization, the known free radical-forming initiators are used in the usual amounts. Water soluble azo initiators, such as alkali metal salts of azo-bis-cyanovalerianic acid, are particularly suitable. Stable dispersions having solids contents up to 60 percent by weight can be prepared at the polymerization temperatures, which are for example between 40° C. and 100° C. Preferably, the content of solids is between 30 percent and 60 percent by weight. The dispersions have a milky white appearance and react neutrally to weakly basically. The viscosity in a typical case is from 20 to 5000 mPa.s.

The aqueous system which is to be thickened can already be acid and, then, thickens rapidly after admixture with the dispersion. In general, it is preferred to mix the aqueous system under neutral or alkaline conditions with the dispersion and then first to acidify it. For acidification, every organic or inorganic acid of sufficient acidity can be employed. Mineral acids, particularly phosphoric acid, are usually most suitable.

A particularly important field of use of the invention is for the thickening of aqueous synthetic resin dispersions. Such dispersions may be acid because of the method by which they are made or are made acid for the purpose of hardening a condensation resin contained therein. Examples of such acid-condensable resins are the water insoluble aminoplast resins and emulsion polymers principally comprising acrylic acid esters or methacrylic acid esters, styrene, or vinyl esters, which contain units of amides or N-methylolamides. In the acid region, these condense between each other or with aminoplast resins. Cationically emulsified resins or resins having cationic groups can also make operation in the acid region necessary, so that thickening also must be effected in this region. Pigment printing pastes comprising water are often acidified and, thus, can be thickened according to the present invention.

Inorganic aqueous systems for etching stainless steel, phosphatizing baths, soldering pastes, acid cleaning agent solutions or pastes, acid depilatories or hair dressing creams, cosmetics, fabric softeners, hydrophobizing agents, silicone emulsions, cataphoretic lacquers, and bleaching pastes are all examples of further aqueous systems which can be thickened according to the present invention to facilitate their handling in particular technical uses or for the improvement of their efficacy.

In slurries of solids, the thickening agents can be used in order to avoid or delay demixing. Often, thickening is necessary for particular working methods. In many cases, a slight thickening, to about 100 to 1,000 mPa.s, is sufficient for aqueous systems which, for example, are to be used for impregnation, soaking, or padding. In other cases, for example for coating pastes and printing pastes, highly thickened systems having viscosities above 2,500 mPa.s are needed. Typical viscosities for pastes of this type are from 5,000 to 15,000 mPa.s.

The aqueous systems to be thickened can contain dissolved polymers or binders such as polyacrylic acid or its salts, polyvinyl alcohol, polyacrylamide, or water-soluble aminoplast resins. Surprisingly, the emulsion polymers are compatible with many polyanionic compounds despite their cationic character.

As a rule, the aqueous dispersions of emulsion polymers according to the present invention are used as such, optionally after dilution with water, for the thickening of aqueous systems. However, at least some of the emulsion polymers according to the present invention can also be used as thickening agents in the form of a finely divided powder. For this purpose, the originally prepared aqueous dispersion is dried under the most protective conditions possible. In such a process, temperatures above the softening temperature of the emulsion polymer are avoided so that on drying the original latex particles are preserved or in any case are only so loosely aggregated that they can be redispersed when stirred into water. Freeze drying and spray drying come first into consideration as drying methods. The powdered polymer obtained can be added just like the aqueous dispersion for thickening purposes. It is recommended to add the powder to a neutral or weakly alkaline aqueous system and to acidify only after it has been uniformly distributed. It is still more advantageous first to redisperse the powder in water and to work further with the material in this form.

In a given particular case, the compatibility of a thickening agent according to the present invention with the remaining components of the aqueous system to be thickened should be tested before the thickening agent is used. If the aqueous system is first adjusted to a pH value below 7 after addition of the thickening agent, the compatibility of the thickening agent at the initial pH value must be taken into consideration as well as compatibility at the final pH value.

The thickening agents according to the present invention are of polycationic nature and, as a result thereof, are capable of exchange effects with anionic, and particularly with polyanionic, compounds. This is true, for example, for anionic surface active agents, dissolved or dispersed polyanionic resins, solids having anionic surface charge, etc. In disadvantage cases, a precipitation, flocculation, or coagulation can occur. Such can often be avoided if the system to be thickened, or the thickening agent, or both, contain a non-ionic surface active agent or protective colloid. However, the thickened systems often prove stable, event without additives of this type.

A better understanding of the present invention and of its many advantages will be had by referring to the following specific Examples, given by way of illustration.

EXAMPLES 1–7

(A) Preparation of the Thickening Dispersions

A solution of one part by weight of the reaction product of 1 mol of isononyl phenol and 100 mols of ethyleneoxide, as an emulsifier, in 240 parts by weight of water is warmed to 80° C. in a reaction vessel equipped with a stirrer, reflux condenser, and thermometer and combined with 0.3 part by weight of the sodium salt of 4,4'-azobis-(4-cyanovalerianic acid). Subsequently, an emulsion previously prepared from 360 parts by weight of water, 29 parts by weight of the aforementioned emulsifier, 0.1 part by weight of the aforementioned azo initiator, and the monomer mixture described below is run into the vessel over a period of two hours. After introduction of the emulsion is concluded, the mixture is permitted to post-react for one hour at 80° C. and is then cooled to room temperature. A dispersion free of coagulate and having a solids content of about 40 percent is obtained.

The monomer mixtures have the following composition in parts by weight:

| | | |
|---|---|---|
| 1. | 51.5 | butyl acrylate |
| | 207.2 | ethyl acrylate |
| | 111.0 | dimethylaminopropyl methacrylate |
| | 0.3 | glycol dimethacrylate |
| 2. | 136.9 | butyl acrylate |
| | 81.5 | ethyl acrylate |
| | 111.0 | dimethylaminopropyl methacrylate |
| | 37.0 | 2-hydroxyethyl methacrylate |
| 3. | 55.2 | butyl acrylate |
| | 222.0 | ethyl acrylate |
| | 92.5 | dimethylaminoisopropyl methacrylate |
| | 0.3 | glycol dimethacrylate |
| 4. | 207.2 | methyl acrylate |
| | 33.3 | 2-ethylhexyl acrylate |
| | 129.5 | diethylaminopropyl acrylate |
| 5. | 129.5 | methyl acrylate |
| | 129.5 | ethyl acrylate |
| | 111.0 | dimethylaminobutyl methacrylate |
| 6. | 25.9 | butyl acrylate |
| | 233.1 | methyl acrylate |
| | 111.0 | 2-(4-morpholinyl)ethyl methacrylate |
| 7. | 55.9 | methyl acrylate |
| | 14.0 | butyl acrylate |
| | 30.0 | N—(3-dimethylamino-2,2-dimethylpropyl) methacrylamide |
| | 0.075 | ethylene glycol dimethacrylate |
| 7a. | 136.9 | butyl acrylate |
| | 81.5 | ethylacrylate |
| | 111.0 | dimethylaminopropyl methacrylate |
| | 20.0 | acrylamide |
| 7b. | 136.9 | butyl acrylate |
| | 81.5 | ethyl acrylate |
| | 111.0 | dimethylaminopropyl methacrylate |
| | 20.0 | methacrylamide |
| 7c. | 136.9 | butyl acrylate |
| | 81.5 | ethyl acrylate |
| | 111.0 | dimethylaminopropyl methacrylate |
| | 20.0 | N—vinyl pyrrolidone |

(B) Intrinsic Thickening

The thickener dispersion is diluted with water to dry solids content of 5 percent and is adjusted to a pH value of 4.5 with 10 percent phosphoric acid. The mixture is white at the beginning and clarifies on thickening within a few minutes. The resulting viscosity is measured with a Brookfield viscosimeter and is given in the following Table.

(C) Thickening of an Organic Acid 20 ml of thickener dispersions 2 and 6 are added with stirring to 100 ml of a 20 percent aqueous propionic acid solution having a pH value of 2.4. The pH climbs to 3.4. After ten minutes, the viscosity reaches its final value, which is given in the following Table.

(D) Thickening of Aqueous Synthetic Dispersions

Two aqueous dispersions, A and B, are adjusted to a solids content of 50 percent by weight and 100 ml portions thereof are combined in each case with 6 g of thickener dispersions 1, 2 and 6, which have been diluted with water to a solids content of 20 percent. The mixture is then acidified with 3 grams of 10 percent phosphoric acid to a pH between 2.2 and 3. After ten minutes, the viscosity is measured using a Brookfield viscosimeter (spindle IV, 12 rpm, 20° C.) and the value is reported in the following Table.

Thickener dispersions 7a, 7b, and 7c are combined in each case with aqueous dispersion B in the aforementioned amounts and under the aforementioned conditions.

Polymer Compositions of Synthetic Resin Dispersion A

Ethyl acrylate: hydroxymethyl methacrylamide: methacrylamide = 92:5:3 (in parts by weight). Viscosity at 50 percent solids content = 80 mPa.s (Brookfield viscosimeter, spindle I, 30 rpm). pH = 2.7.

Polymer Composition of Synthetic Resin Dispersion B

Butyl acrylate: methyl methacrylate: hydroxyethyl methacrylamide: methacrylamide = 42:52:4:2: (parts by weight).
Viscosity at 60 percent solids content = 2500 mPa.s (Brookfield viscosimeter, spindle II, 6 rpm). pH = 2.2.

| | Viscosity Value (in mPa · s) | | |
|---|---|---|---|
| Thickener Dispersion No. | B. Intrinsic Thickening | C. Thickening of Aqueous Propionic Acid | D. Thickening of Synthetic Resin Dispersions |
| | | | A | B |
| 1 | 4,200 | — | 35,800 | 51,000 |
| 2 | 370,000 | 210,000 | — | 89,300 |
| 3 | 450 | — | — | — |
| 4 | 1,400,000 | — | — | — |
| 5 | 62,100 | — | — | — |
| 6 | 2,000 | 8,000 | 17,000 | 30,200 |
| 7 | 108,000 | — | — | — |
| 7a | 320,000 | — | — | 76,000 |
| 7b | 240,000 | — | — | 60,000 |
| 7c | 180,000 | — | — | 95,000 |

EXAMPLE 8

The surprising differences between the emulsion polymers according to the invention and those which contain units of dimethylaminoethyl methacrylate as the salt-forming groups are made evident in following Tables I and II which report viscosity values of aqueous dispersions after storage times of various lengths at 20° C. The two emulsion polymers compared comprise 30 percent by weight of an aminoalkyl ester of methacrylic acid, 40 percent by weight of methyl acrylate, and 30 percent by weight of ethyl acrylate, have a solids content of 40 percent by weight of ethyl acrylate, have a solids content of 40 percent by weight, and a pH value of 7.0. The aminoalkyl ester of emulsion polymer I is derived from dimethylaminoethanol, whereas emulsion polymer II according to the invention contains a methacrylic acid ester of 3-dimethylamino-2,2-dimethyl-propanol-1.

TABLE I

| | Viscosity of a 40% Dispersion (mPa · s) | |
|---|---|---|
| Standing Time at 20° C. | I | II |
| 0 Days | 11,400 | 10 |
| 2 Days | Paste* | 10 |
| 30 Days | Paste* | 10 |

*Viscosity no longer measurable

The thickening effect of the same dispersions after dilution to a solids content of 5 percent and acidification with phosphoric acid to a pH of 4.5 is evident from following Table II.

TABLE II

| | Viscosity (mPa · s) | |
|---|---|---|
| | I | II |
| at pH 7.0 | <10 | <10 |
| at pH 4.5 | 30,000 | 75,000 |

EXAMPLES 9-23

In each of the following Examples relating to a particularly preferred embodiment, 0.035 part by weight of the reaction product of isononylphenol and 100 mols of ethylene oxide (emulsifier A) and 0.03 part by weight of 4,4'-azobis-(4-cyanovalerianic acid)-sodium salt are dissolved in 62 parts by weight by weight of water at 80° C. in a polymerization vessel equipped with a reflux condenser, stirrer, and thermometer. A previously prepared emulsion containing the amounts of monomers specified in following Table III, together with 0.075 part by weight of glycoldimethacrylate, 93 parts by weight of water, 3 parts by weight of emulsifier A, and 0.01 part by weight of 4,4'-azobis-(4-cyanovalerianic acid)-sodium salt are introduced into this solution during the course of two hours at 80° C. The batch is then held at 80° C. for a further two hours and then cooled to room temperature. A dispersion free of coagulate having a solids content of about 40 percent is obtained.

TABLE III

| | Copolymer Composition (parts by weight) | | | | | | | Viscosity of a 5% aqueous solution of the emulsion polymer after acidification with 10% aqueous phosphoric acid to pH 4.5 | |
|---|---|---|---|---|---|---|---|---|---|
| Example No. | DAM (*DPM) | BA | EA | MA | MMA | GDM | $T_{\lambda max}$ (°C.) | (mPa · s) | Brookfield-Viscosimeter Spindle/rpm |
| 9 | 30 | 70 | | | | 0.075 | −10 | 4,375 | III/6 |
| 10 | 30 | 35 | 35 | | | 0.075 | 0 | 68,500 | IV/6 |
| 11 | 30 | | 30 | 40 | | 0.075 | 10 | 75,000 | IV/6 |
| 12 | 30 | | 70 | | | 0.075 | 5 | 320,000 | IV/1.5 |
| 13 | 25 | | 30 | 45 | | 0.075 | 10 | 18,500 | IV/6 |
| 14 | 35 | | 25 | 40 | | 0.075 | 20 | 1.6 × 10⁶ | IV/0.3 |
| 15 | 30 | | 30 | 40 | | — | 10 | 45,000 | IV/6 |
| 16 | 50 | | 40 | | 10 | 0.075 | 25 | 227,000 | IV/0.3 |
| 17 | 50 | | 30 | | 20 | 0.075 | 40 | 28,300 | IV/6 |
| 18 | 50 | | 20 | | 30 | 0.075 | 60 | 10,800 | IV/6 |
| 19 | 50 | | 25 | | 25 | 0.075 | 50 | 14,500 | IV/6 |
| 20 | 90 | | 10 | | | — | 50 | >2 × 10⁶ | IV/0.3 |
| 21 | 100 | | | | | — | 75 | >2 × 10⁶ | IV/0.3 |
| 22 | 30* | | 30 | 40 | | 0.075 | 5 | 61,300 | IV/6 |

TABLE III-continued

| Example No. | Copolymer Composition (parts by weight) | | | | | | $T_{\lambda max}$ (°C.) | Viscosity of a 5% aqueous solution of the emulsion polymer after acidification with 10% aqueous phosphoric acid to pH 4.5 | |
|---|---|---|---|---|---|---|---|---|---|
| | DAM (*DPM) | BA | EA | MA | MMA | GDM | | (mPa · s) | Brookfield-Viscosimeter Spindle/rpm |
| 23 | 50* | | 20 | 30 | | 0.075 | 55 | 187,000 | IV/0.3 |

DAM = 3-dimethylamino-2,2-dimethylpropyl methacrylate
DPM = 3-dipropylamino-2,2-dimethylpropyl methacrylate
BA = butyl acrylate
EA = ethyl acrylate
MA = methyl acrylate
MMA = methyl methacrylate
GDM = glycol dimethacrylate 8 g of a thickening dispersion according to Example 11 of the foregoing Table III, diluted with water to a solids content of 20 percent, are added with stirring, together with 2 g of 10 percent phosphoric acid, to 100 g of a 50 percent aqueous synthetic resin dispersion having a pH value of 2.7 and a viscosity of 80 mPa.s (Brookfield-Viscosimeter, Spindle I, 30 rpm), the polymer phase of which is composed of 92 percent by weight of ethyl acrylate, 5 percent by weight of N-methylol methacrylamide, and 3 percent by weight of methacrylamide. The viscosity increases rapidly and after ten minutes reaches a value of 62,000 mPa.s (Brookfield-Viscosimeter, Spindle IV, 6 rpm, 25° C.). The pH value of the thickened dispersion is 3.5.

What is claimed is:

1. The method of thickening an aqueous system, which method comprises mixing the aqueous system with an aqueous dispersion, different from said aqueous system, of particles of a synthetic copolymer, free of acid groups, comprising
   (A) 20–100 percent by weight of a basic unsaturated free radically polymerizable monomer having a $pK_b$-value from 3 to 6 and at least one basic nitrogen atom,
   (B) 0–95 percent by weight of a neutral unsaturated free radically polymerizable comonomer which has at most limited solubility in water, and
   (C) 0–30 percent by weight of a neutral unsaturated free radically polymerizable comonomer which is water soluble,
said polymer having a molecular weight of at least 500,000 and being water soluble at a pH value below 7, said mixture of the aqueous system and aqueous dispersion having a pH value below 7, whereby said copolymer is present therein in a dissolved state.

2. A method as in claim 1 wherein said copolymer comprises, as component (A), units of an ester of an α,β-unsaturated polymerizable carboxylic acid, said ester having at least one basic nitrogen atom therein and the alcohol residue of said ester having a total of at least five carbon atoms.

3. A method as in claim 2 wherein said ester is an ester of an alkanol also containing a basic nitrogen atom and having an alkylene group with at least three carbon atoms between the ester oxygen atom thereof and said basic nitrogen atom.

4. A method as in claim 3 wherein the said alkylene group contains at least three carbon atoms in a straight chain between the ester oxygen atom and the basic nitrogen atom.

5. A method as in claim 1 wherein said aqueous system is admixed with such an amount of said aqueous dispersion of synthetic copolymer that a thickening of at least 10 percent is effected in said aqueous system.

6. A method as in claim 5 wherein the amount of aqueous dispersion of synthetic copolymer is such that the thickening effect, calculated as the product of the initial viscosity of the aqueous system and of the percentage thickening, has a value of at least 1,000 mPa.s.

7. A method as in claim 1 wherein said aqueous system is thickened to a viscosity of at least 1,000 mPa.s.

8. A method as in claim 1 wherein said aqueous dispersion of synthetic copolymer is admixed in an amount containing from 0.5 to 10 percent by weight of the synthetic copolymer, calculated on the water portion of the aqueous system.

9. A method as in claim 1 wherein said aqueous system to be thickened contains at least 20 percent by weight of water.

10. A method as in claim 1 wherein said aqueous system is an aqueous dispersion of a synthetic resin.

11. A method as in claim 10 wherein said synthetic resin is self-cross linking under the influence of an acid catalyst.

12. A method as in claim 2 wherein said component (A) is an ester of 3-dialkylamino-2,2-dimethylpropanol.

13. A method as in claim 1 wherein said synthetic compolymer comprises at most 60 percent by weight of component(A).

14. A method as in claim 1 wherein said synthetic copolymer comprises as component (B), at least 20 percent, by total weight of the polymer, of at least one member selected from the group consisting of alkyl esters of acrylic acid and of methacrylic acid, said ester having 1 to 4 carbon atoms in the alkyl portion thereof.

15. A method as in claim 1 wherein said synthetic resin copolymer comprises from 0.01 to 0.5 percent of a crosslinking agent.

* * * * *